(12) United States Patent
Markovitz et al.

(10) Patent No.: US 11,419,537 B2
(45) Date of Patent: Aug. 23, 2022

(54) METHODS AND SYSTEMS FOR RESOLVING CATHETER RENDERING ISSUES

(71) Applicant: St. Jude Medical, Cardiology Division, Inc., St. Paul, MN (US)

(72) Inventors: Craig Markovitz, Leipzig (DE); Louis-Philippe Richer, Quebec (CA); Chunlan Jiang, Crystal, MN (US); Cyrille Casset, Saint Selve (FR); Jan O. Mangual-Soto, Rho (IT); Luke McSpadden, Los Angeles, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 15 days.

(21) Appl. No.: 16/965,422

(22) PCT Filed: Jan. 29, 2019

(86) PCT No.: PCT/US2019/015680
§ 371 (c)(1),
(2) Date: Jul. 28, 2020

(87) PCT Pub. No.: WO2019/152420
PCT Pub. Date: Aug. 8, 2019

(65) Prior Publication Data
US 2021/0076968 A1    Mar. 18, 2021

Related U.S. Application Data

(60) Provisional application No. 62/624,215, filed on Jan. 31, 2018.

(51) Int. Cl.
*A61B 5/00* (2006.01)
*A61B 5/304* (2021.01)
(Continued)

(52) U.S. Cl.
CPC .............. *A61B 5/304* (2021.01); *A61B 5/287* (2021.01); *A61B 5/339* (2021.01); *A61B 5/7475* (2013.01)

(58) Field of Classification Search
CPC ......... A61B 5/304; A61B 5/339; A61B 5/287; A61B 5/7475; A61B 5/276; A61B 2560/0276; A61B 5/061; A61B 5/367
See application file for complete search history.

(56) References Cited

U.S. PATENT DOCUMENTS 9,522,048 B1 * 12/2016 Schmit .................... A61B 5/304
2003/0028118 A1    2/2003 Dupree et al.

FOREIGN PATENT DOCUMENTS

WO    2016183468 A1    11/2016
WO    2017192775 A1    11/2017

OTHER PUBLICATIONS

International Search Report and Written Opinion for PCT/2019/015680, dated Apr. 4, 2019, 15 pps.

* cited by examiner

*Primary Examiner* — Scott M. Getzow
(74) *Attorney, Agent, or Firm* — Armstrong Teasdale LLP

(57) ABSTRACT

Systems and methods for resolving catheter rendering issues are provided. A system includes a catheter including a plurality of electrodes and a plurality of catheter pins, each catheter pin corresponding to an associated electrode. The system further includes a mapping system communicatively coupled to the catheter, the mapping system including a pin box including a plurality of sockets, a display device configured to render the catheter, and an electronic control unit (ECU). The ECU is configured to determine that the catheter is being rendered incorrectly on the display device, determine a number of electrodes that are being rendered incorrectly on the display device, identify at least one particular (Continued)

electrode of the plurality of electrodes that is being rendered incorrectly on the display device, and attempt to resolve the incorrect rendering of the catheter based on the determined number of electrodes and the at least one particular electrode.

20 Claims, 11 Drawing Sheets

(51) Int. Cl.
    *A61B 5/339*     (2021.01)
    *A61B 5/287*     (2021.01)

METHODS AND SYSTEMS FOR RESOLVING CATHETER RENDERING ISSUES

CROSS REFERENCE TO RELATED APPLICATIONS

This application is the national stage entry of PCT/US2019/015680, filed on Jan. 29, 2019, which claims the benefit of priority to U.S. provisional application Ser. No. 62/624,215, filed Jan. 31, 2018, both of which are incorporated herein by reference in their entirety.

FIELD OF THE DISCLOSURE

This disclosure relates to systems and methods for imaging patient anatomy using a catheter, and more particularly, this disclosure relates to computer-implemented systems and methods for resolving catheter rendering issues.

BACKGROUND

It is known that various computer-based systems and computer-implemented methodologies can be used to generate multi-dimensional surface models of geometric structures, such as, for example, anatomic structures. More specifically, a variety of systems and methods have been used to generate multi-dimensional surface models of the heart and/or particular portions thereof.

The human heart muscle routinely experiences electrical currents traversing its many surfaces and ventricles, including the endocardial chamber. Just prior to each heart contraction, the heart muscle is said to "depolarize" and "repolarize," as electrical currents spread across the heart and throughout the body. In healthy hearts, the surfaces and ventricles of the heart will experience an orderly progression of a depolarization wave. In unhealthy hearts, such as those experiencing atrial arrhythmia, including for example, ectopic atrial tachycardia, atrial fibrillation, and atrial flutter, the progression of the depolarization wave may not be so orderly. Arrhythmias may persist as a result of scar tissue or other obstacles to rapid and uniform depolarization. These obstacles may cause depolarization waves to repeat a circuit around some part of the heart. Atrial arrhythmia can create a variety of dangerous conditions, including irregular heart rates, loss of synchronous atrioventricular contractions, and stasis of blood flow, all of which can lead to a variety of ailments and even death.

Medical devices, such as, for example, electrophysiology (EP) catheters, are used in a variety of diagnostic and/or therapeutic medical procedures to correct such heart arrhythmias. Typically in a procedure, a catheter is manipulated through a patient's vasculature to a patient's heart, for example, and carries one or more electrodes that may be used for mapping, ablation, diagnosis, and/or to perform other functions. Once at an intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to, from, and at the treatment site, which can invariably be a function of a user's skill level.

Before or during an ablation procedure, however, a user must measure and diagnose these undesirable electrical pathways and regions of arrhythmia "breakout." An electrogram, used to help identify these regions, is any record of change in electric potential over time, often obtained by placing an electrode directly on or near the surface of the heart tissue. To acquire electrograms, conventional techniques include point-by-point methods of recording changes in electrical potential. These changes in potential may then be mapped, using a mapping system, onto a corresponding model of an anatomical structure. In other words, these methods enable the creation of electrocardiographic maps by navigating one or more catheters around an area of interest and collecting electrogram and spatial localization data from one spot to the next and then mapping the collected data accordingly.

In such systems, to ensure proper operation, the catheter should be properly connected to the mapping system. Otherwise, the catheter and anatomy observed using the catheter may be incorrectly rendered on a display device. For example, faulty electrodes may cause the catheter to be incorrectly rendered. Further, the catheter generally includes a plurality of catheter pins that are plugged into corresponding sockets on a pin box. However, the catheter may be incorrectly rendered if one or more catheter pins are plugged into the incorrect socket.

Incorrect connections are further compounded in that, during initial setup, it is generally not immediately apparent that a catheter pin is plugged into the incorrect socket. Instead, the issue may not be detected until the catheter has been placed within a patient's heart, requiring medical personnel to stop the current procedure and troubleshoot the rendering issue. This is generally undesirable, as it increases the overall time for the procedure and may frustrate medical personnel.

BRIEF SUMMARY OF THE DISCLOSURE

In one embodiment, the present disclosure is directed to a system including a catheter including a plurality of electrodes and a plurality of catheter pins, each catheter pin corresponding to an associated electrode of the plurality of electrodes, and a mapping system communicatively coupled to the catheter. The mapping system includes a pin box including a plurality of sockets corresponding to the plurality of catheter pins, a display device configured to render the catheter, and an electronic control unit (ECU) communicatively coupled to the display device and the pin box. The ECU is configured to determine that the catheter is being rendered incorrectly on the display device, determine a number of electrodes that are being rendered incorrectly on the display device, identify at least one particular electrode of the plurality of electrodes that is being rendered incorrectly on the display device, and attempt to resolve the incorrect rendering of the catheter based on the determined number of electrodes and the at least one particular electrode.

In another embodiment, the present disclosure is directed to a computer-implemented method for resolving catheter rendering issues in a system including a catheter having a plurality of electrodes and a plurality of catheter pins, each catheter pin corresponding to an associated electrode of the plurality of electrodes. The system further includes a mapping system including a pin box including a plurality of sockets corresponding to the plurality of catheter pins, a display device configured to render the catheter, and an electronic control unit (ECU) communicatively coupled to the display device and the pin box. The method includes determining, by the ECU, that the catheter is being rendered incorrectly on the display device, determining, by the ECU, a number of electrodes that are being rendered incorrectly on the display device, identifying, by the ECU, at least one particular electrode of the plurality of electrodes that is being rendered incorrectly on the display device, and attempting, by the ECU, to resolve the incorrect rendering of the catheter based on the determined number of electrodes and the at least one particular electrode.

In another embodiment, the present disclosure is directed to a processing apparatus for resolving catheter rendering issues in a system including a catheter having a plurality of electrodes and a plurality of catheter pins, each catheter pin corresponding to an associated electrode of the plurality of electrodes. The system further includes a mapping system including a pin box including a plurality of sockets corresponding to the plurality of catheter pins, and a display device configured to render the catheter. The processing apparatus is communicatively coupled to the display device and the pin box and is configured to determine that the catheter is being rendered incorrectly on the display device, determine a number of electrodes that are being rendered incorrectly on the display device, identify at least one particular electrode of the plurality of electrodes that is being rendered incorrectly on the display device, and attempt to resolve the incorrect rendering of the catheter based on the determined number of electrodes and the at least one particular electrode.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
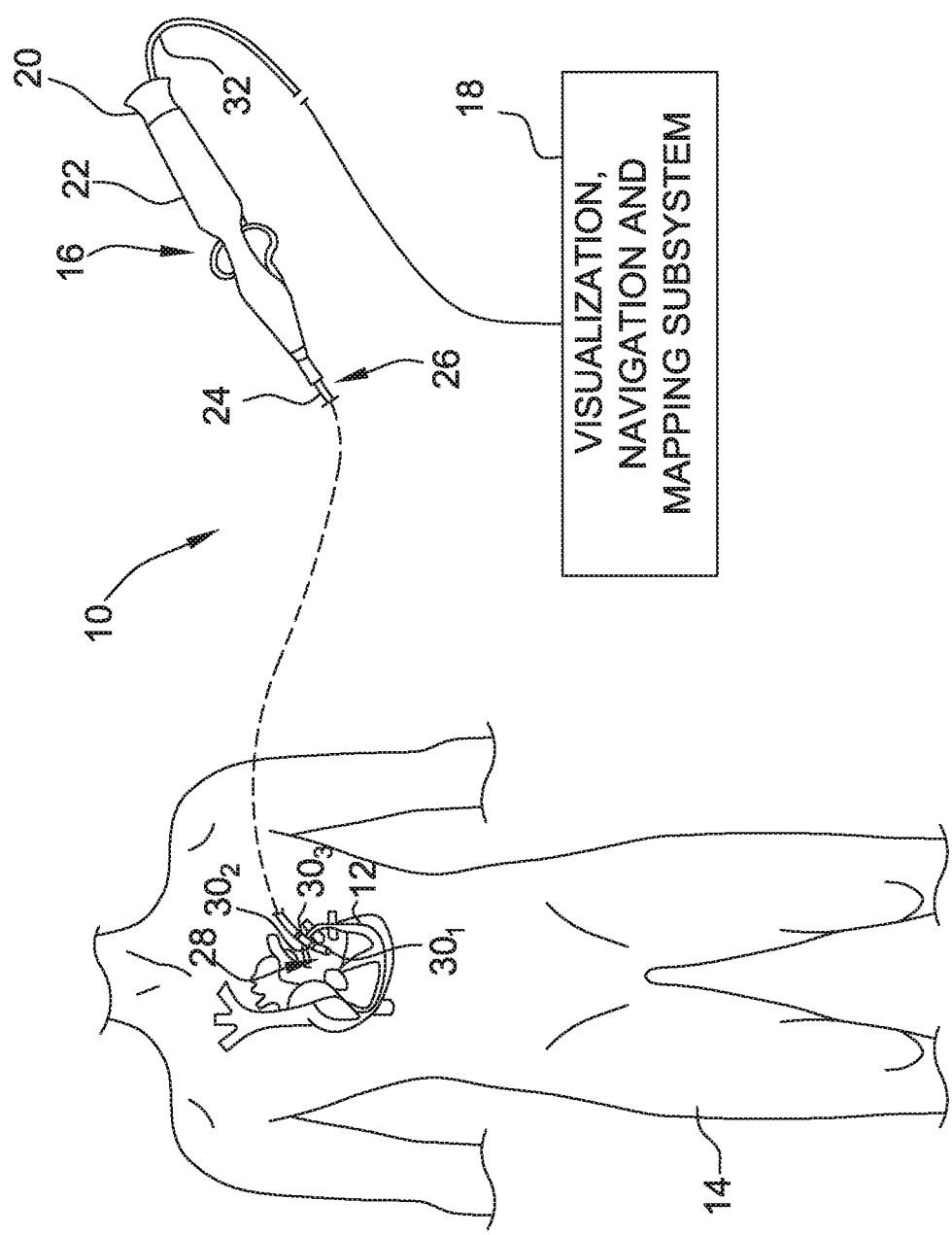
FIG. 1 is a schematic and diagrammatic view of a system for performing at least one of a diagnostic and a therapeutic medical procedure in accordance with present teachings.

The disclosure provides systems and methods for automatically correcting catheter rendering issues caused by faulty electrodes or connection issues between catheter pins and a pin box of a mapping system. In the embodiments described herein, an electronic control unit determines that a catheter is being rendered improperly on a display device, and automates troubleshooting the catheter rendering issues Referring now to the drawings wherein like reference numerals are used to identify identical components in the various views, FIG. 1 illustrates one exemplary embodiment of a system 10 for performing one or more diagnostic and/or therapeutic functions on or for a tissue 12 of a body 14. In an exemplary embodiment, tissue 12 includes heart or cardiac tissue within a human body 14. It should be understood, however, that system 10 may find application in connection with a variety of other tissues within human and non-human bodies, and therefore, the present disclosure is not meant to be limited to the use of system 10 in connection with only cardiac tissue and/or human bodies.

System 10 may include a medical device (e.g., a catheter 16) and a subsystem 18 for the visualization, navigation, and/or mapping of internal body structures (hereinafter referred to as the "visualization, navigation, and mapping subsystem 18", "subsystem 18", or "mapping system").

In this embodiment, medical device includes a catheter 16, such as, for example, an electrophysiology catheter. In other exemplary embodiments, medical device may take a form other than catheter 16, such as, for example and without limitation, a sheath or catheter-introducer, or a catheter other than an electrophysiology catheter. For clarity and illustrative purposes only, the description below will be limited to embodiments of system 10 wherein medical device is a catheter (catheter 16).

Catheter 16 is provided for examination, diagnosis, and/or treatment of internal body tissues such as tissue 12. Catheter 16 may include a cable connector 20 or interface, a handle 22, a shaft 24 having a proximal end 26 and a distal end 28 (as used herein, "proximal" refers to a direction toward the end of catheter 16 near handle 22, and "distal" refers to a direction away from handle 22), and one or more sensors, such as, for example and without limitation, a plurality of electrodes 30 (i.e., $30_1$, $30_2$, . . . , $30_N$), mounted in or on shaft 24 of catheter 16 at or near distal end 28 of shaft 24. The sensors may include, for example, impedance electrodes.

In this embodiment, each electrode 30 is configured to both acquire electrophysiological (EP) data corresponding to tissue 12, and to produce signals indicative of its three-dimensional (3-D) position (hereinafter referred to as "positioning data"). In another embodiment, catheter 16 may include a combination of electrodes 30 and one or more positioning sensors (e.g., electrodes other than electrodes 30 or magnetic sensors (e.g., coils)). In one such embodiment, electrodes 30 are configured to acquire EP data relating to tissue 12, while the positioning sensor(s) is configured to generate positioning data indicative of the 3-D position thereof, which may be used to determine the 3-D position of each electrode 30. In other embodiments, catheter 16 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Connector 20 provides mechanical and electrical connection(s) for one or more cables 32 extending, for example, from visualization, navigation, and mapping subsystem 18 to one or more electrodes 30 or the positioning sensor(s) mounted on catheter 16. In other embodiments, connector 20 may also provide mechanical, electrical, and/or fluid connections for cables extending from other components in system 10, such as, for example, an ablation system and a fluid source (when catheter 16 includes an irrigated catheter). Connector 20 is disposed at proximal end 26 of catheter 16.

Handle 22 provides a location for a user to hold catheter 16 and may further provide means for steering or guiding shaft 24 within body 14. For example, handle 22 may include means to manipulate one or more steering wires extending through catheter 16 to distal end 28 of shaft 24 to steer shaft 24. It will be appreciated by those of skill in the art that the construction of handle 22 may vary. In other embodiments, the control of catheter 16 may be automated such as by being robotically driven or controlled, or driven and controlled by a magnetic-based guidance system. Accordingly, catheters controlled either manually or automatically are both within the spirit and scope of the present disclosure.

Shaft 24 is an elongate, tubular, and flexible member configured for movement within body 14. Shaft 24 supports, for example and without limitation, electrodes 30, other electrodes or positioning sensors mounted thereon, associated conductors, and possibly additional electronics used for signal processing or conditioning. Shaft 24 may also permit transport, delivery and/or removal of fluids (including irrigation fluids, cryogenic ablation fluids, and body fluids), medicines, and/or surgical tools or instruments. Shaft 24, which may be made from conventional materials such as polyurethane, defines one or more lumens configured to house and/or transport electrical conductors, fluids, or surgical tools. Shaft 24 may be introduced into a blood vessel or other structure within body 14 through a conventional introducer. Shaft 24 may then be steered or guided through body 14 to a desired location such as tissue 12.

Distal end 28 of shaft 24 may be the main portion of catheter 16 that contains electrodes 30 or other sensors for acquiring EP data and positioning data. As described above, in one embodiment, electrodes 30 may be configured to acquire both EP data and positioning data. In another embodiment, and as will be described in greater detail below, electrodes 30 may be configured to acquire EP data while one or more positioning sensors may be configured to acquire positioning data, which may then be used to determine the respective positions of electrodes 30. Regardless of whether the positioning data is acquired by electrodes 30 or by positioning sensors, distal end 28 may be arranged in a number of configurations that facilitate the efficient acquisition, measurement, collection, or the like of EP data from tissue 12.

Figure 2:
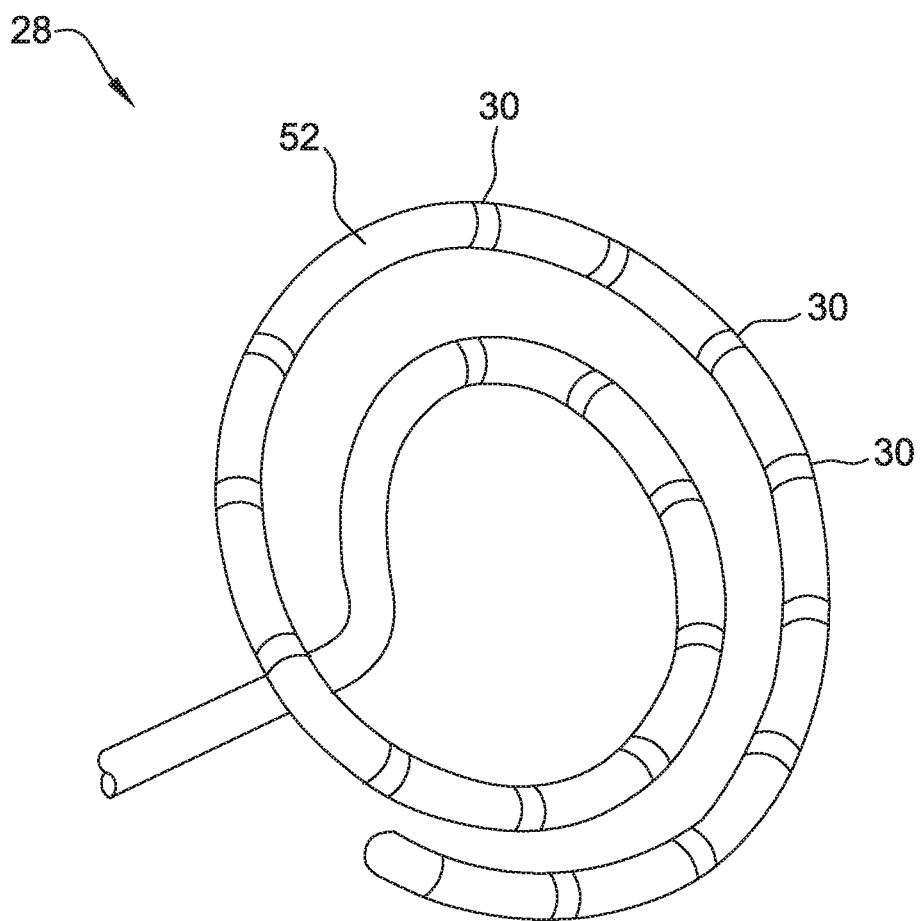
FIG. 2 is an isometric view of a distal end of one embodiment of a medical device arranged in a spiral configuration.

In one embodiment, as shown in FIG. 2, distal end 28 may be arranged in a spiral configuration. In this embodiment, the spiral configuration may be generally planar and may contain a high density of electrodes 30 for taking unipolar or bipolar measurements of EP data from tissue 12. Unipolar measurements may generally represent the electrical voltage perceived at each electrode. Bipolar measurements, though, may generally represent the electrical potential between any pair of electrodes. And as one skilled in the art will recognize, bipolar measurements may be computed from unipolar measurements. Moreover, electrodes 30 may be disposed in or along distal end 28 in a known spatial configuration such that the distances between electrodes 30 are known. The diameters of the loops, such as loop 52, may vary from one embodiment to another. In one embodiment, the diameter of the outermost loop is twenty millimeters. In an alternative embodiment, the spiral configuration may contain multiple spiral loops.

There are many advantages to placing a high density of electrodes 30 on the spiral configuration or at distal end 28 of catheter 16. Because the distribution of electrodes 30 is dense, and because of the multitude of possible unipolar and bipolar comparisons of electrodes 30, the spiral configuration may be ideal for creating high definition (HD) surface maps representative of electrical activity on tissue 12.

Figure 3:
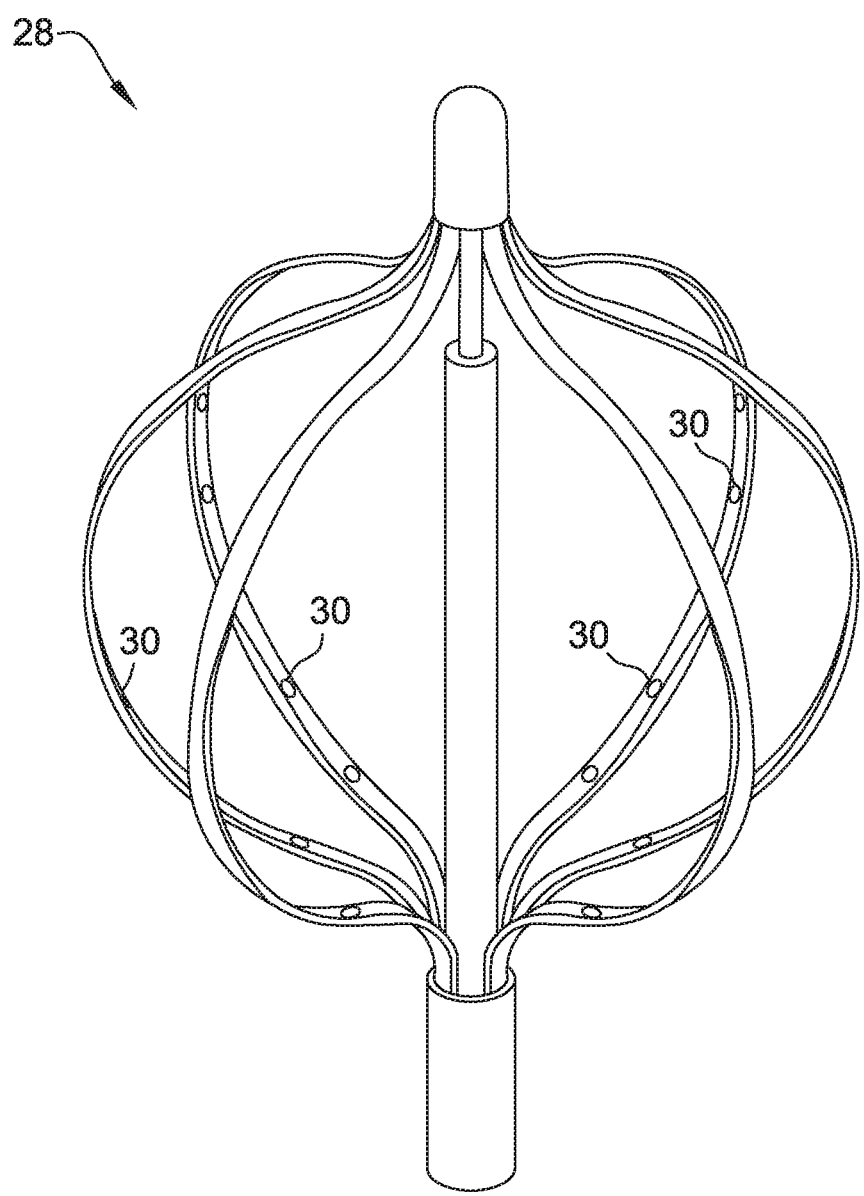
FIG. 3 is an isometric view of a distal end of another embodiment of a medical device arranged in a basket configuration.

In another embodiment, as shown in FIG. 3, distal end 28 may be arranged in a basket configuration. The basket configuration, or a similar configuration with a generally cylindrical array of electrodes 30, may contain a high density of electrodes 30. In one embodiment, electrodes 30 may be non-contact electrodes that generally need not be in contact with tissue 12 to measure EP data. In another embodiment, electrodes 30 may include both contact and non-contact electrodes.

Such non-contact electrodes may be used for unipolar analyses. It may be advantageous to analyze unipolar EP data since a unipolar electrogram morphology may provide more information regarding colliding wavefronts (presence of "R" waves in the QRS Complex known in the art), short radius reentry wavefronts (presence of the sinusoid waveform), and source wavefronts (a "QS" morphology on the electrogram at the onset of depolarization). In general, a depolarization wavefront is a group of electrical vectors that traverse tissue 12 of body 14. Depolarization wavefronts may vary in pattern, size, amplitude, speed, and the like. And some depolarization wavefronts may be relatively orderly while others may be relatively, or even entirely, disorderly.

In another embodiment, however, bipolar EP data may provide better spatial localization data, better depolarization wave directionality indications, and better alternating current (AC) electrical noise rejection. With bipolar EP data, a pair of electrodes 30 (commonly referred to as "poles" or "bi-poles") may be spaced apart, but positioned relatively close together with respect to electric fields caused by other remote parts of body 14. Thus, effects from remote electric fields may be negated since electrodes 30 are positioned close to one another and experience similar effects from the distant electric field.

Figure 4A:
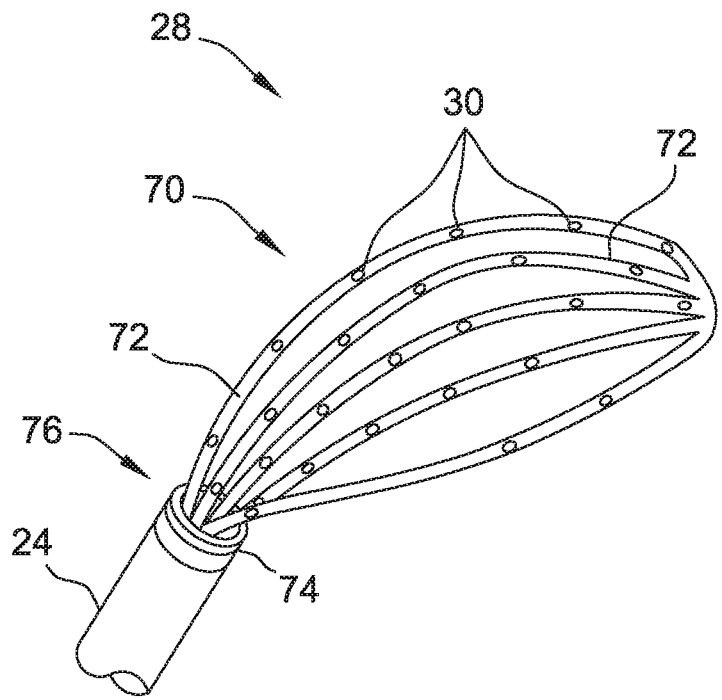
FIGS. 4A and 4B are isometric and side views, respectively, of a distal end of one embodiment of a medical device arranged in a matrix-like configuration.
Figure 4B:
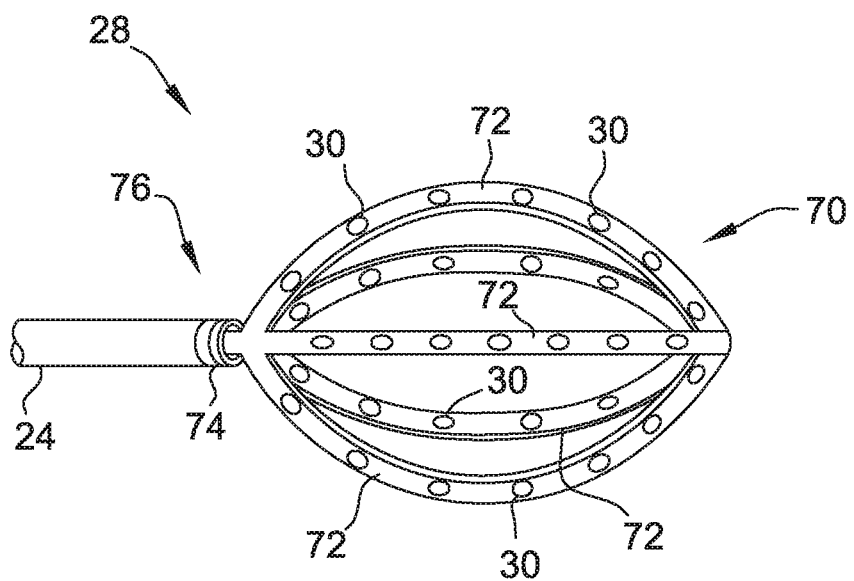

In yet another embodiment of the distal end 28 shown in FIGS. 4A and 4B, a matrix-like configuration may also be provided with a high density of electrodes 30. FIG. 4A shows an isometric view of the matrix-like configuration, while FIG. 4B shows a side view. The matrix-like configuration may have a number of splines 72 arranged side by side, with each spline 72 having at least one electrode 30 mounted thereon. Longer splines may contain more electrodes 30 to maintain a consistent electrode density throughout the matrix-like configuration.

In the embodiment shown in FIGS. 4A and 4B, the matrix-like configuration may be cupped, almost as if to have a slight scoop as seen in FIG. 4A. In another embodiment (not shown), the matrix-like configuration may be substantially flat or planar, without any scoop-like feature. While both embodiments may facilitate data measurements from tissue 12, the matrix-like configuration shown in FIG.

4A in particular may be used to acquire at least some non-contact measurements. Another possible use of the matrix-like configuration would be to help diagnose arrhythmias and direct epicardial ablation therapies in the pericardial space.

In one embodiment, the matrix-like configuration along with other configurations of distal end 28 may collapse to a streamlined profile for insertion, manipulation, and removal from body 14. In addition, or in the alternative, distal end 28 may be at least partially concealed and transported within shaft 24 when not collecting data or performing a procedure. Shaft 24 may be more streamlined than distal end 28, and therefore may provide a better vehicle for transporting distal end 28 to and from tissue 12. Once at the intended site, distal end 28 may be deployed from shaft 24 to perform the intended procedures. Likewise, after the procedures are performed, distal end 28 may be re-concealed, at least in part, within shaft 24 for removal from body 14.

One exemplary way in which the matrix-like configuration is collapsible into a streamlined profile or fully or partially deployable is to allow outer splines 72 to translate modestly within shaft 24 while anchoring innermost splines 72 to shaft 24 at a point 74 at distal end 28 thereof. Moreover, for enhanced functionality, a joint 76 may be incorporated near point 74, either for providing flexibility or for selectively deflecting distal end 28, thereby allowing distal end 28 better access to tissue 12.

Figure 5:
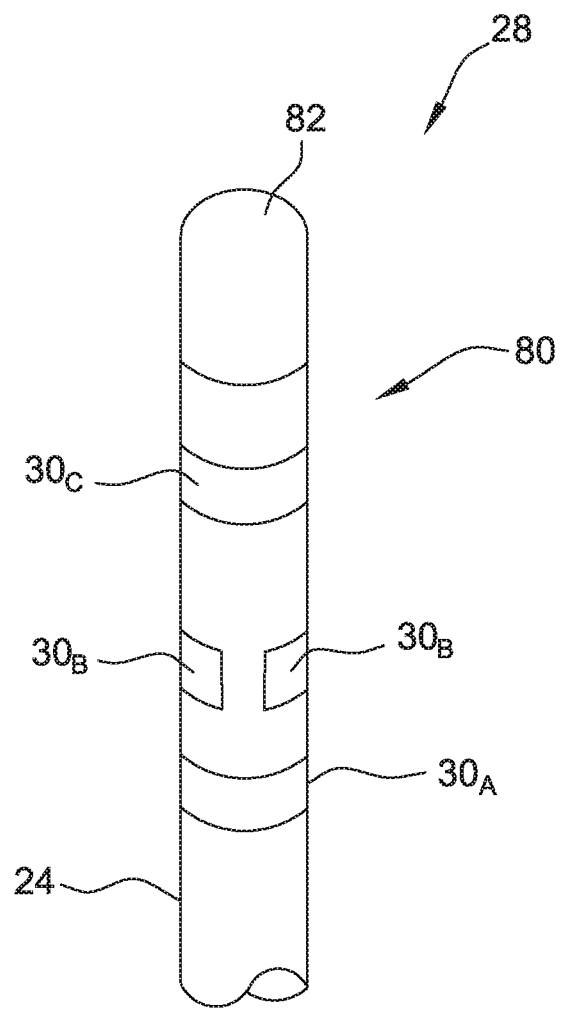
FIG. 5 is a top view of a distal end of one embodiment of a medical device wherein the medical device is a radio frequency (RF) ablation catheter.

Another exemplary embodiment of a high-density electrode catheter is illustrated in FIG. 5. In this embodiment, distal end 28 includes an ablation tip 80, and may be well suited for enhancing radio frequency (RF) ablation procedures. More particularly, the arrangement may allow for the provision of rapid positioning feedback and may also enable updates to be made to HD surface maps as the ablative procedures are being performed.

With continued reference to FIG. 5, in an exemplary embodiment wherein visualization, navigation, and mapping subsystem 18 is an electric field-based system, distal end 28 may include a proximal ring electrode $30_A$ positioned close to, yet spaced apart from, a series of spot or button electrodes $30_B$. Proximal ring electrode $30_A$ and spot electrodes $30_B$ may be used to acquire both EP data and positioning data. Spaced further distally from the spot electrodes $30_B$, a distal ring electrode $30_C$ may be disposed in or on shaft 24 so that bipolar measurements of EP data may be made between the spot electrodes $30_B$ and the distal ring electrode $30_C$. Finally, distal end 28 further includes an ablation electrode 82 for performing ablation therapies, such as, for example and without limitation, RF ablation therapies.

Visualization, navigation, and mapping subsystem 18 may determine the positions of proximal ring electrode $30_A$ (or a geometric center thereof), the spot electrodes $30_B$, and distal ring electrode $30_C$ (or a geometric center thereof) in the same manner as the position(s) of the electrode(s) 30 shown in FIG. 6, as will be described in greater detail below. Based on these positions and/or the known configuration of distal end 28 (e.g., the spacing of the various electrodes), the position of ablation electrode 82 may also be determined and, in certain embodiments, projected onto a geometrical anatomical model.

By incorporating at least three non-co-linear electrodes as is illustrated, for example, in FIG. 5, rotational information about distal end 28 (referred to as "orientation") may be calculated. Hence six degrees of freedom (three for position and three for orientation) may be determined for ablation tip 80 of catheter 16. Knowing the position and orientation of distal end 28 allows for a much simpler registration of coordinates into a body coordinate system, as opposed to a coordinate system with respect to the catheter itself.

In some embodiments, visualization, navigation, and mapping subsystem 18 includes a magnetic field-based system. For example visualization, navigation, and mapping subsystem 18 may include an electrical field- and magnetic field-based system such as the EnSite™ Precision™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 28 may include at least one magnetic field sensor—e.g., magnetic coils (not shown). If two or more magnetic field sensors are disposed near ablation electrode 82, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In yet another embodiment of distal end 28 illustrated in FIG. 5, distal ring electrode $30_C$ may be omitted and spot electrodes $30_B$ may be located in its place. As a result, spot electrodes $30_B$ would be closer to ablation electrode 82, which would provide positioning coordinates closer to ablation electrode 82. This in turn may provide for more accurate and precise calculation of the position of ablation electrode 82. Additionally, just as if the distal ring electrode $30_C$ were still in place, a mean signal from the spot electrodes $30_B$ and the proximal ring electrode $30_A$ could still be used to obtain bipolar EP data.

Figure 6:
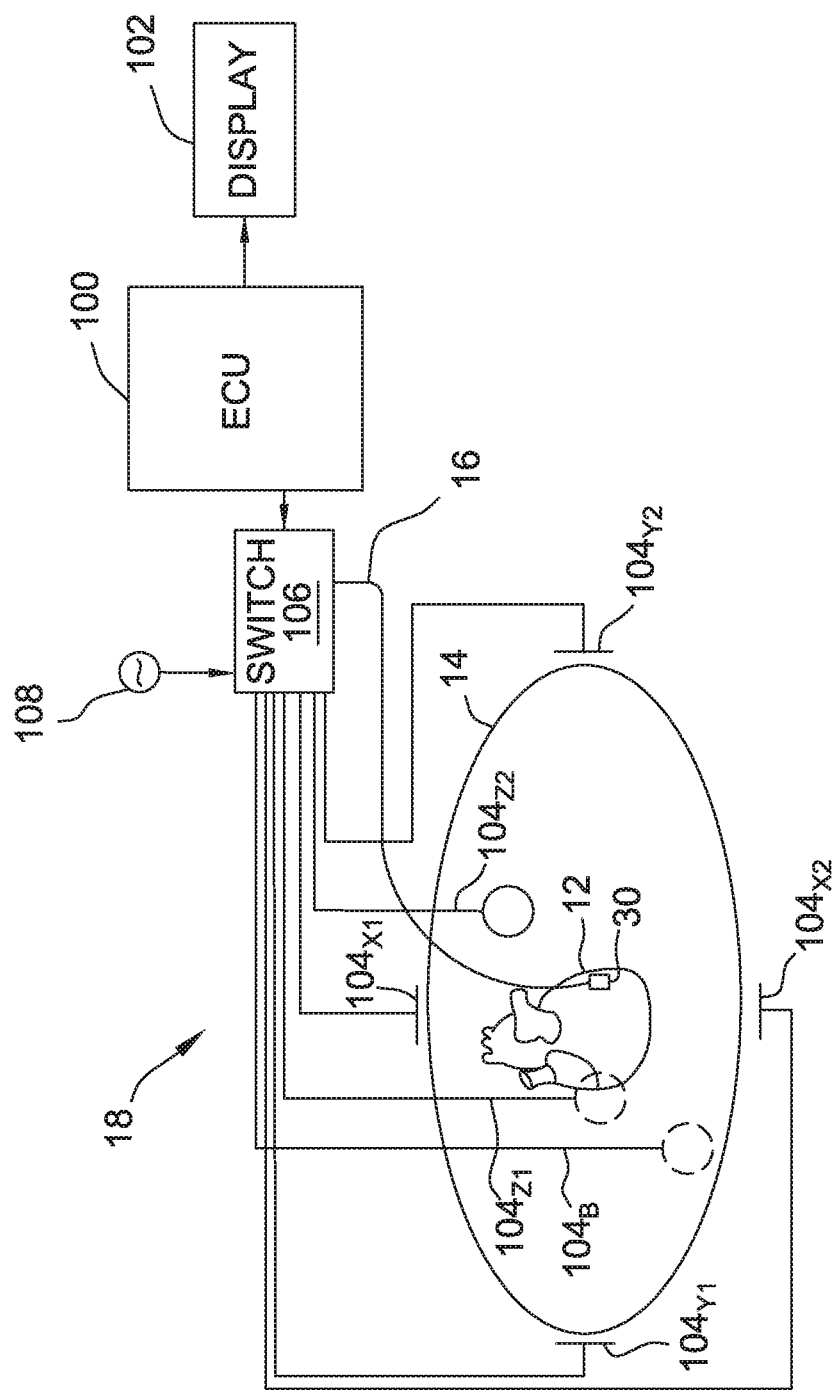
FIG. 6 is a schematic and diagrammatic view of one embodiment of a visualization, navigation, and mapping subsystem that may be used with the system shown in FIG. 1

With reference to FIGS. 1 and 6, the visualization, navigation, and mapping subsystem 18 will now be described. The visualization, navigation, and mapping subsystem 18 is provided for visualization, navigation, and/or mapping of internal body structures and/or medical devices. In an exemplary embodiment, the subsystem 18 may contribute to the functionality of the system 10 in two principal ways. First, the subsystem 18 may provide the system 10 with a geometrical anatomical model representing at least a portion of the tissue 12. Second, the subsystem 18 may provide a means by which the position coordinates (x, y, z) of the electrodes 30 (or generally, sensors) may be determined as they measure EP data for analyses performed as part of the system 10. In certain embodiments, positioning sensors (e.g., electrical-field based or magnetic-field based) that are fixed relative to the electrodes 30 are used to determine the position coordinates. The positioning sensors provide the subsystem 18 with positioning data sufficient to determine the position coordinates of the electrodes 30. In other embodiments, position coordinates may be determined from the electrodes 30 themselves by using, for example, voltages measured by the electrodes 30.

Visualization, navigation, and mapping subsystem 18 may utilize an electric field-based system, such as, for example, the ENSITE NAVX™ system commercially available from Abbott Laboratories, and as generally shown with reference to U.S. Pat. No. 7,263,397 titled "Method and Apparatus for Catheter Navigation and Location and Mapping in the Heart," the entire disclosure of which is incorporated herein by reference, or the ENSITE VELOCITY™ system running a version of the NAVX™ software.

In other exemplary embodiments, subsystem 18 may utilize systems other than electric field-based systems. For example, subsystem 18 may comprise a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, subsystem 18 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, subsystem 18 may utilize a combination electric field-based and magnetic field-based system as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the subsystem 18 may comprise or be used in conjunction with other commonly available systems, such as, for example and without limitation, fluoroscopic, computed tomography (CT), and magnetic resonance imaging (MRI)-based systems.

In one embodiment wherein subsystem 18 includes an electric field-based system, and as described above, catheter 16 includes a plurality of electrodes 30 configured to both acquire EP data and produce signals indicative of catheter position and/or orientation information (positioning data). Subsystem 18 may use, for example and without limitation, time-division multiplexing or other similar techniques such that positioning data indicative of the position of electrodes 30 is measured intermittently with EP data. Thus, an electric field used to locate electrodes 30 may be activated between measurements of EP data, and electrodes 30 may be configured to measure both EP data and the electric field from subsystem 18, though at different times.

In other embodiments, however, wherein electrodes 30 may not be configured to produce positioning data, catheter 16 may include one or more positioning sensors in addition to electrodes 30. In one such embodiment, catheter 16 may include one or more positioning electrodes configured to generate signals indicative of the 3-D position or location of the positioning electrode(s). Using the position of the positioning electrode(s) along with a known configuration of catheter 16 (e.g., the known spacing between the positioning electrode(s) and electrodes 30) the position or location of each electrode 30 can be determined.

Alternatively, in another embodiment, rather than including an electric-field based system, subsystem 18 includes a magnetic field-based system. In such an embodiment, catheter 16 may include one or more magnetic sensors (e.g., coils) configured to detect one or more characteristics of a low-strength magnetic field. The detected characteristics may be used, for example, to determine a 3-D position or location for the magnetic sensors(s), which may then be used with a known configuration of the catheter 16 to determine a position or location for each electrode 30.

For purposes of clarity and illustration only, subsystem 18 will be described hereafter as comprising an electric field-based system, such as, for example, the ENSITE NAVX™ or VELOCITY™ systems identified above. Further, the description below will be limited to an embodiment of system 10 wherein electrodes 30 are configured to both acquire EP data and produce positioning data. It will be appreciated in view of the above, however, that the present disclosure is not meant to be limited to an embodiment wherein subsystem 18 includes an electric field-based system or electrodes 30 serve a dual purpose or function. Accordingly, embodiments wherein subsystem 18 is other than an electric field-based system, and catheter 16 includes positioning sensors in addition to electrodes 30 remain within the spirit and scope of the present disclosure.

With reference to FIGS. 1 and 6, in this embodiment subsystem 18 may include an electronic control unit (ECU) 100 and a display device 102. Alternatively, one or both of ECU 100 and display device 102 may be separate and distinct from, but electrically connected to and configured for communication with, subsystem 18. Subsystem 18 may still further include a plurality of patch electrodes 104, among other components. With the exception of a patch electrode $104_B$ called a "belly patch," patch electrodes 104 are provided to generate electrical signals used, for example, in determining the position and orientation of catheter 16, and in the guidance thereof. Catheter 16 may be coupled to ECU 100 or subsystem 18 with a wired or wireless connection.

In one embodiment, patch electrodes 104 are placed orthogonally on the surface of body 14 and are used to create axes-specific electric fields within body 14. For instance, patch electrodes $104_{X1}$, $104_{X2}$ may be placed along a first (x) axis. Patch electrodes $104_{Y1}$, $104_{Y2}$ may be placed along a second (y) axis, and patch electrodes $104_{Z1}$, $104_{Z2}$ may be placed along a third (z) axis. These patches may act as a pair or dipole. In addition or in the alternative, the patches may be paired off an axis or paired in series, e.g., $104_{X1}$ is paired with $104_{Y1}$, then $104_{Y2}$, $104_{Z1}$, $104_{Z2}$. In addition, multiple patches may be placed on one axis, e.g., under the patient. Each of the patch electrodes 104 may be coupled to a multiplex switch 106. In this embodiment, ECU 100 is configured, through appropriate software, to provide control signals to switch 106 to thereby sequentially couple pairs of electrodes 104 to a signal generator 108. Excitation of each pair of electrodes 104 generates an electric field within body 14 and within an area of interest such as tissue 12. Voltage levels at the non-excited electrodes 104, which are referenced to the belly patch $104_B$, are filtered and converted and provided to ECU 100 for use as reference values.

With electrodes 30 electrically coupled to ECU 100, electrodes 30 are placed within electrical fields that patch electrodes 104 create in body 14 (e.g., within the heart) when patch electrodes 104 are excited. Electrodes 30 experience voltages that are dependent on the respective locations between patch electrodes 104 and the respective positions of electrodes 30 relative to tissue 12. Voltage measurement comparisons made between electrodes 30 and patch electrodes 104 can be used to determine the position of each electrode 30 relative to tissue 12. Accordingly, ECU 100 is configured to determine position coordinates (x, y, z) of each electrode 30. Further, movement of electrodes 30 near or against tissue 12 (e.g., within a heart chamber) produces information regarding the geometry of tissue 12.

The information relating to the geometry of the tissue 12 may be used, for example, to generate models and/or maps of anatomical structures that may be displayed on a display device, such as, for example, display device 102. Information received from electrodes 30 can also be used to display on display device 102 the location and orientation of the electrodes 30 and/or the tip of catheter 16 relative to tissue 12. Accordingly, among other things, ECU 100 may provide a means for generating display signals for display device 102 and for creating a graphical user interface (GUI) on display device 102. It should be noted that in some instances where the present disclosure refers to objects as being displayed on the GUI or display device 102, this may actually mean that representations of these objects are being displayed on GUI or the display device 102.

It should also be noted that while in an exemplary embodiment ECU 100 is configured to perform some or all of the functionality described above and below, in another exemplary embodiment, ECU 100 may be separate and distinct from subsystem 18, and subsystem 18 may have another ECU configured to perform some or all of the functionality described herein. In such an embodiment, that ECU could be electrically coupled to, and configured for communication with, ECU 100. However, for purposes of clarity and illustration only, the description below will be limited to an embodiment wherein ECU 100 is shared between subsystem 18 and system 10 and is configured to perform the functionality described herein. Still further, despite reference to a "unit," ECU 100 may include a number or even a considerable number of components (e.g., multiple units, multiple computers, etc.) for achieving the exemplary functions described herein. In some embodiments, then, the present disclosure contemplates ECU 100 as encompassing components that are in different locations.

ECU 100 may include, for example, a programmable microprocessor or microcontroller, or may comprise an application specific integrated circuit (ASIC). ECU 100 may include a central processing unit (CPU) and an input/output (I/O) interface through which ECU 100 may receive a plurality of input signals including, for example, signals generated by patch electrodes 104 and positioning sensors. ECU 100 may also generate a plurality of output signals including, for example, those used to control display device 102 and switch 106. ECU 100 may be configured to perform various functions, such as those described in greater detail above and below, with appropriate programming instructions or code. Accordingly, in one embodiment, ECU 100 is programmed with one or more computer programs encoded on a computer-readable storage medium for performing the functionality described herein.

In addition to the above, ECU 100 may further provide a means for controlling various components of system 10 including, but not limited to, switch 106. In operation, ECU 100 generates signals to control switch 106 to thereby selectively energize patch electrodes 104. ECU 100 receives positioning data from catheter 16 reflecting changes in voltage levels and from the non-energized patch electrodes 104. ECU 100 uses the raw positioning data produced by patch electrodes 104 and electrodes 30, and corrects the data to account for respiration, cardiac activity, and other artifacts using known or hereinafter developed techniques. The corrected data, which comprises position coordinates corresponding to each of electrodes 30 (e.g., (x, y, z)), may then be used by ECU 100 in a number of ways, such as, for example and without limitation, to create a geometrical anatomical model of an anatomical structure or to create a representation of catheter 16 that may be superimposed on a map, model, or image of tissue 12 generated or acquired by ECU 100.

ECU 100 may be configured to construct a geometrical anatomical model of tissue 12 for display on display device 102. ECU 100 may also be configured to generate a GUI through which a user may, among other things, view a geometrical anatomical model. ECU 100 may use positioning data acquired from electrodes 30 or other sensors on distal end 28 or from another catheter to construct the geometrical anatomical model. In one embodiment, positioning data in the form of a collection of data points may be acquired from surfaces of tissue 12 by sweeping distal end 28 of catheter 16 along the surfaces of tissue 12. From this collection of data points, ECU 100 may construct the geometrical anatomical model. One way of constructing the geometrical anatomical model is described in U.S. patent application Ser. No. 12/347,216 entitled "Multiple Shell Construction to Emulate Chamber Contraction with a Mapping System," the entire disclosure of which is incorporated herein by reference. Moreover, the anatomical model may comprise a 3-D model or a two-dimensional (2-D) model. As will be described in greater detail below, a variety of information may be displayed on the display device 102, and in the GUI displayed thereon, in particular, in conjunction with the geometrical anatomical model, such as, for example, EP data, images of catheter 16 and/or electrodes 30, metric values based on EP data, HD surface maps, and HD composite surface maps. Catheter 16 may be visually rendered on display device 102 using, for example, the systems and methods described in U.S. Pat. No. 9,560,988 entitled "System and Method for Rendering an Image of an Elongate Medical Device", the disclosure of which is incorporated herein by reference in its entirety.

To display the data and images that are produced by ECU 100, display device 102 may include one or more conventional computer monitors other display devices well known in the art. It is desirable for display device 102 to use hardware that avoids aliasing. To avoid aliasing, the rate at which display device 102 is refreshed should be at least as fast as the frequency with which ECU 100 is able to continuously compute various visual aids, such as, for example, HD surface maps.

As described above, the plurality of electrodes 30 disposed at distal end 28 of catheter 16 are configured to acquire EP data. The data collected by the respective electrodes 30 may be collected simultaneously. In one embodiment, EP data may include at least one electrogram. An electrogram indicates the voltage measured at a location (e.g., a point along tissue 12) over a period of time. By placing a high density of electrodes 30 on distal end 28, ECU 100 may acquire a set of electrograms measured from adjacent locations in tissue 12 during the same time period. The adjacent electrode 30 locations on distal end 28 may collectively be referred to as a "region."

ECU 100 may also acquire times at which electrograms are measured, the positions from which electrograms are measured, and the distances between electrodes 30. As for timing data, ECU 100 may track, maintain, or associate timing data with the voltages of each electrode 30 as measured. In addition, the 3-D position coordinates of each electrode 30 as it measures voltages may be determined, for example, as described above by visualization, navigation, and mapping subsystem 18. ECU 100 may be configured to continuously acquire position coordinates of electrodes 30, especially when electrodes 30 are measuring EP data. Because ECU 100 may know the spatial distribution of electrodes 30 of each distal end 28 configuration (e.g., matrix-like, spiral, basket, etc.), ECU 100 may recognize from the position coordinates of electrodes 30 which configuration of distal end 28 is deployed within a patient. Furthermore, the distances between electrodes 30 may be known by ECU 100 because electrodes 30 may be precisely and strategically arranged in a known spatial configuration.

Thus, if distal end 28 is not deformed, a variety of analyses may use the known distances between electrodes 30 without having to obtain the coordinate positions from the subsystem 18 to solve for the distances between electrodes 30.

With ECU 100 having voltage, timing, and position data corresponding to respective electrodes 30 in addition to the known electrode 30 spatial configuration, many comparative temporal and spatial analyses may be performed, as described below. Some of these analyses lead to creation of HD surface maps representing activation patterns from tissue 12, which are possible in part because of the high density of electrodes 30 at distal end 28 of shaft 24. By providing a high density of electrodes at distal end 28, the accuracy and resolution of HD surface maps produced by system 10 are enhanced.

With respect to capturing or collecting EP data measured by the high density of electrodes 30, in one embodiment, ECU 100 may be programmed to continuously record and analyze data in real-time or near real-time. In another embodiment, a user may specify through a user input device a time window (e.g., 200 ms, 30 seconds, 10 minutes etc.) during which ECU 100 may capture data measured from electrodes 30. The user input device may include, for example and without limitation, a mouse, a keyboard, a touch screen, and/or the like. It should be noted that in one embodiment, electrodes 30 may continuously measure voltages along tissue 12, and ECU 100 may selectively capture or record such voltages from electrodes 30. In still another embodiment, electrodes 30 measure voltages in accordance with a sampling rate or command from ECU 100. Once distal end 28 of shaft 24 is positioned near or along tissue 12 as desired, the user could prompt a trigger for the time window. The user may configure the trigger for the time window to correspond, for example, to a particular cardiac signal or the expiration of a timer. To illustrate, trigger could be set so ECU 100 records data from electrodes 30 before, during, and after an arrhythmia breakout or disappearance. One possible way to capture the data occurring just prior to the particular cardiac signal would be to use a data buffer that stores data (which may later be obtained) for an amount of time.

ECU 100 may be configured to recognize particular cardiac signals to trigger the time window. To that end, electrodes 30 may constantly measure EP data when positioned near tissue 12. This may be the case even if the user has not prompted the trigger for the time window. For example, ECU 100 may recognize that distal end 28 is near tissue 12 inside body 14 based on the continuous measurements in the range of voltages that are expected near tissue 12. Or ECU 100 may, for example, be configured to constantly monitor voltages from electrodes 30 when ECU 100 is powered "on." In any event, ECU 100 may continuously acquire EP data and continuously assess patterns and characteristics in the EP data. For example, metrics based on EP data include, for example, local activation time (LAT), depolarization amplitude voltage (e.g., peak-to-peak amplitude (PP)), complex fractionated electrogram (CFE) activity, dominant frequency (DF), Fast Fourier Transform (FFT) ratio, activation potential, diastolic potential, and late potential. U.S. Pat. No. 9,186,081 entitled "System and Method for Diagnosing Arrhythmias and Directing Catheter Therapies", the disclosure of which is incorporated herein by reference in its entirety, discloses multiple examples of metrics based on EP data.

To ensure proper operation, catheter 16 should be properly connected to subsystem 18. Otherwise, catheter 16 may be incorrectly rendered on display device 102. In some cases, faulty electrodes 30 may cause catheter 16 to be incorrectly rendered. For example, electrodes 30 may be damaged when hospitals sterilize and re-use catheters 16.

Further, catheter 16 generally includes a plurality of catheter pins that are plugged into corresponding sockets on a pin box to couple catheter 16 to subsystem 18. However, catheter 16 may be incorrectly rendered on display device 102 if one or more catheter pins are plugged into the incorrect socket or disconnected. For example, for proper operation, in some embodiments, twenty different catheter pins must be plugged into the correct sockets (as defined by a virtual pin box controlled by ECU 100). This may be relatively difficult, as the persons plugging in the catheter pins may be medical personnel that are focused on, among other items, the patient's well-being.

Incorrect connections are further compounded in that, during initial setup, it is generally not immediately apparent that a catheter pin is plugged into the incorrect socket. Instead, the issue will likely not be detected until catheter 16 has been placed within a patient's heart, at which point the incorrect catheter rendering (e.g., distortion, an incomplete image, etc.) will be observed. This requires medical personnel to stop the current procedure and troubleshoot the rendering issue (e.g., by looking at an EP recording system, switching pins in the pin box, etc.). While the rendering issue can usually be resolved relatively quickly, it increases the overall time for the procedure and may frustrate medical personnel.

Accordingly, the embodiments described herein provide systems and methods for automatically correcting catheter rendering issues caused by faulty electrodes 30 or connection issues between catheter 16 and the pin box. Specifically, in the embodiments described herein, ECU 100 automates troubleshooting of catheter rendering issues, as described herein.

Figure 7:
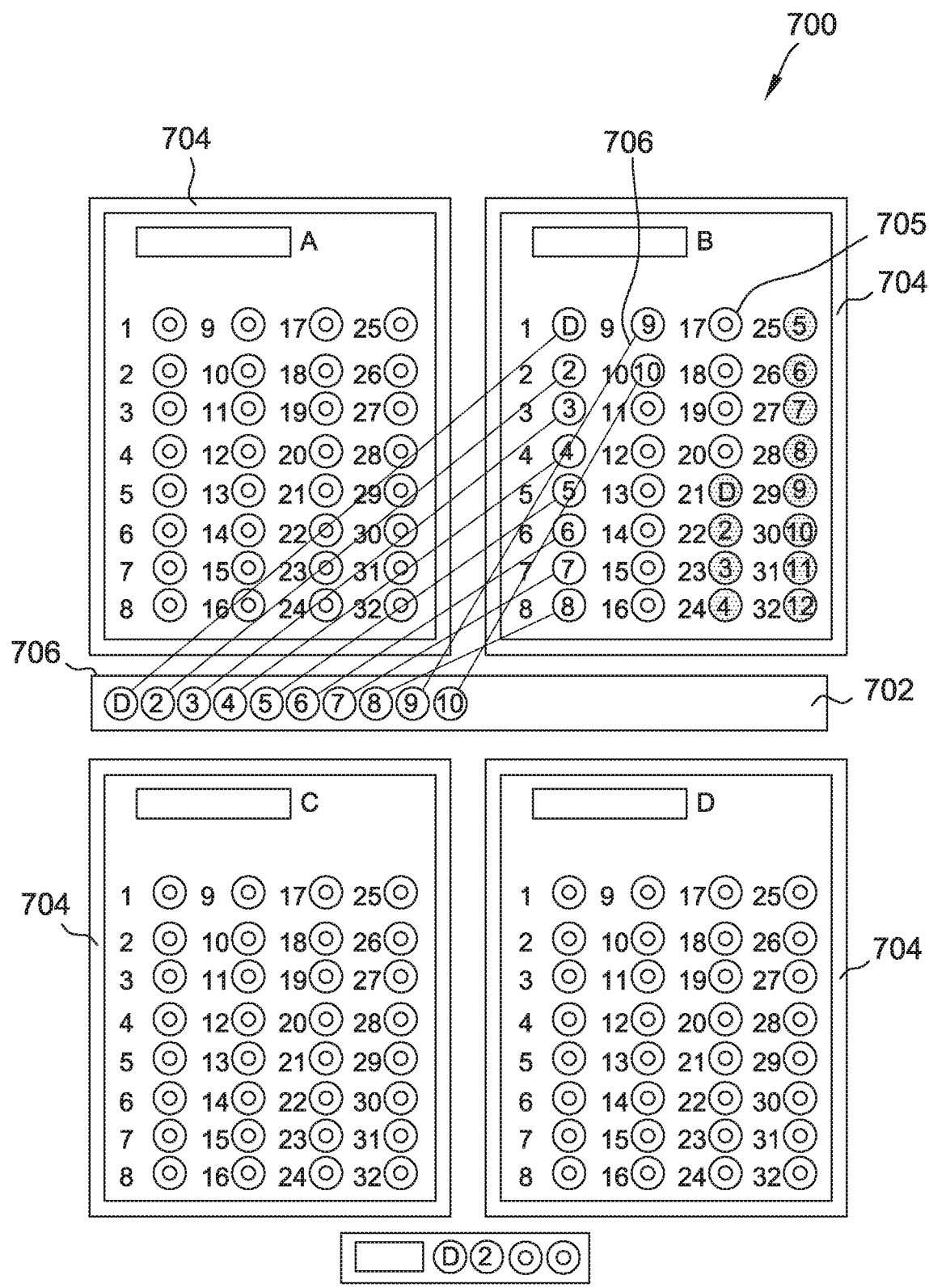
FIG. 7 is a screenshot of an example display that may be displayed on a display device of the visualization, navigation, and mapping subsystem shown in FIG. 6.

FIG. 7 is a screenshot of an example display 700 that may be displayed on display device 102. As shown in FIG. 7, display 700 includes a catheter virtual representation 702 (corresponding to catheter 16) and a pin box virtual representation 704 (corresponding to the pin box) including a plurality of sockets 705. Further, display 700 shows connections 706 between catheter virtual representation 702 and pin box virtual representation 704. Connections 706 indicate the current arrangement of connections between the catheter pins of catheter 16 and sockets on the pin box. In this embodiment, there are ten connections 706 between the catheter pins of catheter 16 and sockets on the pin box. Alternatively, there may be any number of connections between the catheter pins of catheter 16 and sockets 705 on the pin box. Further, in this embodiment, although catheter 16 is connected to a single pin box, multiple pin box virtual representations 704 are shown on display 700. Alternatively, in some embodiments, only a single pin box virtual representation 704 is shown.

Initially, in the embodiments described herein, ECU 100 determines that catheter 16 is being rendered incorrectly. For example, in some embodiments, ECU 100 determines that catheter 16 is being rendered incorrectly in response to a user input made at ECU 100 (e.g., by a user that observes the incorrectly rendered catheter 16 on display device 102). Alternatively, in some embodiments, ECU 100 is capable of automatically determining that catheter 16 is incorrectly rendered. For example, ECU 100 may compare a shape of the rendered catheter on display device 102 to an expected catheter shape, and may determine that catheter 16 is incorrectly rendered if the rendered catheter shape is substantially different than the expected catheter shape.

ECU 100 subsequently determines a number of electrodes 30 that are being rendered incorrectly. Similar to determining that catheter 16 is being rendered incorrectly, ECU 100 may determine the number of incorrectly rendered electrodes 30 based on a user input or automatically (e.g., by performing image analysis on the rendered catheter on display device 102). Further, ECU 100 determines (again, based on user input or automatically) which particular electrodes 30 are being rendered incorrectly. ECU 100 then troubleshoots the catheter rendering issue depending on the number of incorrectly rendered electrodes 30, as described herein.

Figure 8:
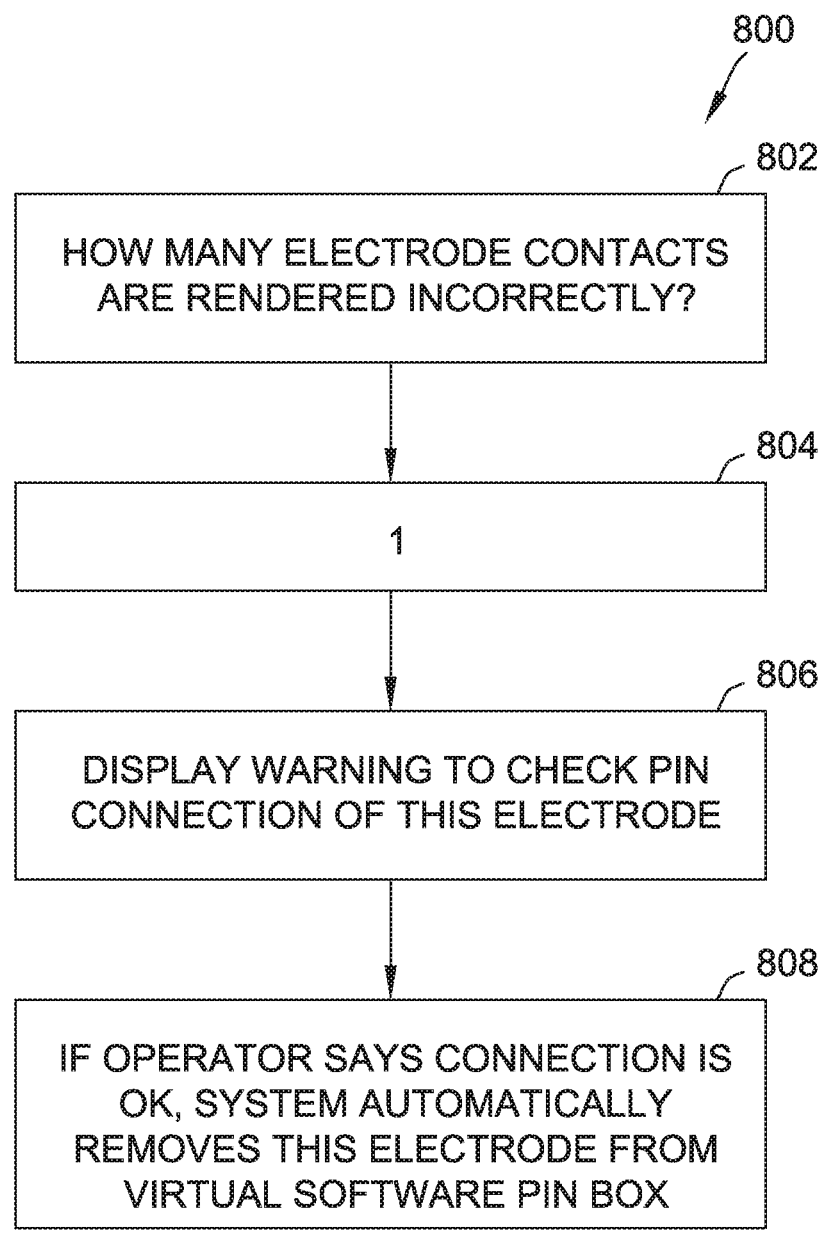
FIG. 8 is a flowchart of a method for automatically troubleshooting a catheter rendering issue when one electrode is being rendered incorrectly.

FIG. 8 is a flowchart of a method 800 for automatically troubleshooting a catheter rendering issue when one electrode 30 is being rendered incorrectly. As shown in FIG. 8, ECU 100 initially determines 802 how many electrodes 30 rendered incorrectly, and makes 804 the determination that a single electrode 30 is rendered incorrectly.

In response, ECU 100 generates and displays 806 a warning on display device 102. The warning instructs a human operator to check or verify the connection between the catheter pin and the socket associated with the incorrectly rendered electrode 30. For example, upon checking, the operator may determine that the catheter pin for the particular electrode 30 is not currently plugged into the correct socket for the particular electrode 30. Accordingly, the operator may proceed to plug the catheter pin into the correct socket, resolving the rendering issue.

If, however, the operator verifies that the catheter pin for the particular electrode 30 is currently connected properly (e.g., by user input to ECU 100), it is likely that the particular electrode 30 is faulty, and unlikely that the catheter pin is plugged into the incorrect socket or disconnected. Accordingly, in this situation, ECU 100 automatically removes 808 the particular electrode 30 and corresponding catheter pin from the virtual pin box (i.e., corresponding to the physical pin box and controlled by ECU 100), such that the particular electrode 30 is no longer used when rendering catheter 16.

Figure 9:
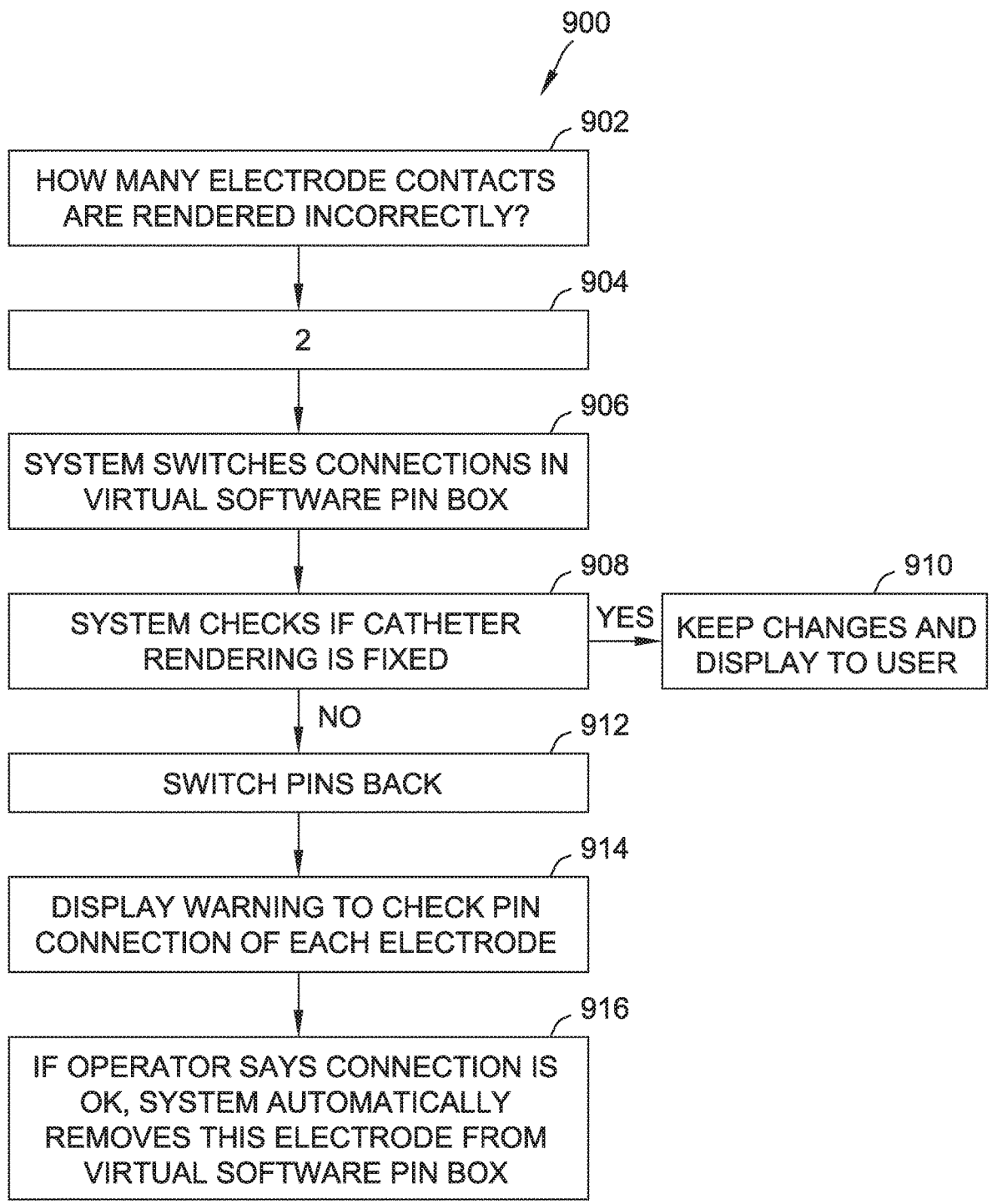
FIG. 9 is a flowchart of a method for automatically troubleshooting a catheter rendering issue when two electrodes are being rendered incorrectly.

FIG. 9 is a flowchart of a method 900 for automatically troubleshooting a catheter rendering issue when two electrodes 30 are being rendered incorrectly. As shown in FIG. 9, ECU 100 initially determines 902 how many electrodes 30 rendered incorrectly, and makes 904 the determination that two electrodes 30 are rendered incorrectly.

When two electrodes 30 are rendered incorrectly, it is likely that the catheter pins for the two electrodes 30 are switched relative to the sockets for those two electrodes 30. Accordingly, ECU 100 automatically switches 906 the connections for those two sockets in the virtual pin box. That is, the catheter pins remain physically connected to the same sockets, but ECU 100 controls the virtual pin box to electronically switch the functions of the two sockets.

ECU 100 subsequently checks 908 to see if the rendering issue has been resolved by switching 906 (e.g., based on user input or automatically). If the rendering issue is resolved, ECU 100 maintains 910 the changes to the virtual pin box, displays the changes (e.g., on display device 102) and method 900 ends.

If the rendering issue is not resolved by switching 906, ECU 100 switches 912 the connections back in the virtual pin box, and displays 914 a warning on display device 102. The warning instructs the operator to check the connections between the catheter pin and the socket associated with each of the two incorrectly rendered electrodes 30. For example, upon checking, the operator may determine that the catheter pins for each of the two electrodes 30 are disconnected or otherwise faulty. Accordingly, the operator may proceed to fix the connections for one or two of the two electrodes 30, partially or fully resolving the rendering issue.

If, however, the operator verifies that the catheter pin for at least one of the two electrodes 30 is connected properly (e.g., by user input to ECU 100), it is likely that the at least one electrode 30 of the two electrodes 30 is faulty, and unlikely that the catheter pin is plugged into the incorrect socket for the at least one electrode 30 of the two electrodes 30. Accordingly, in this situation, ECU 100 automatically removes 916 the at least one electrode 30 of the two electrodes 30 from the virtual pin box, such that the at least one electrode 30 is no longer used when rendering catheter 16.

Figure 10A:
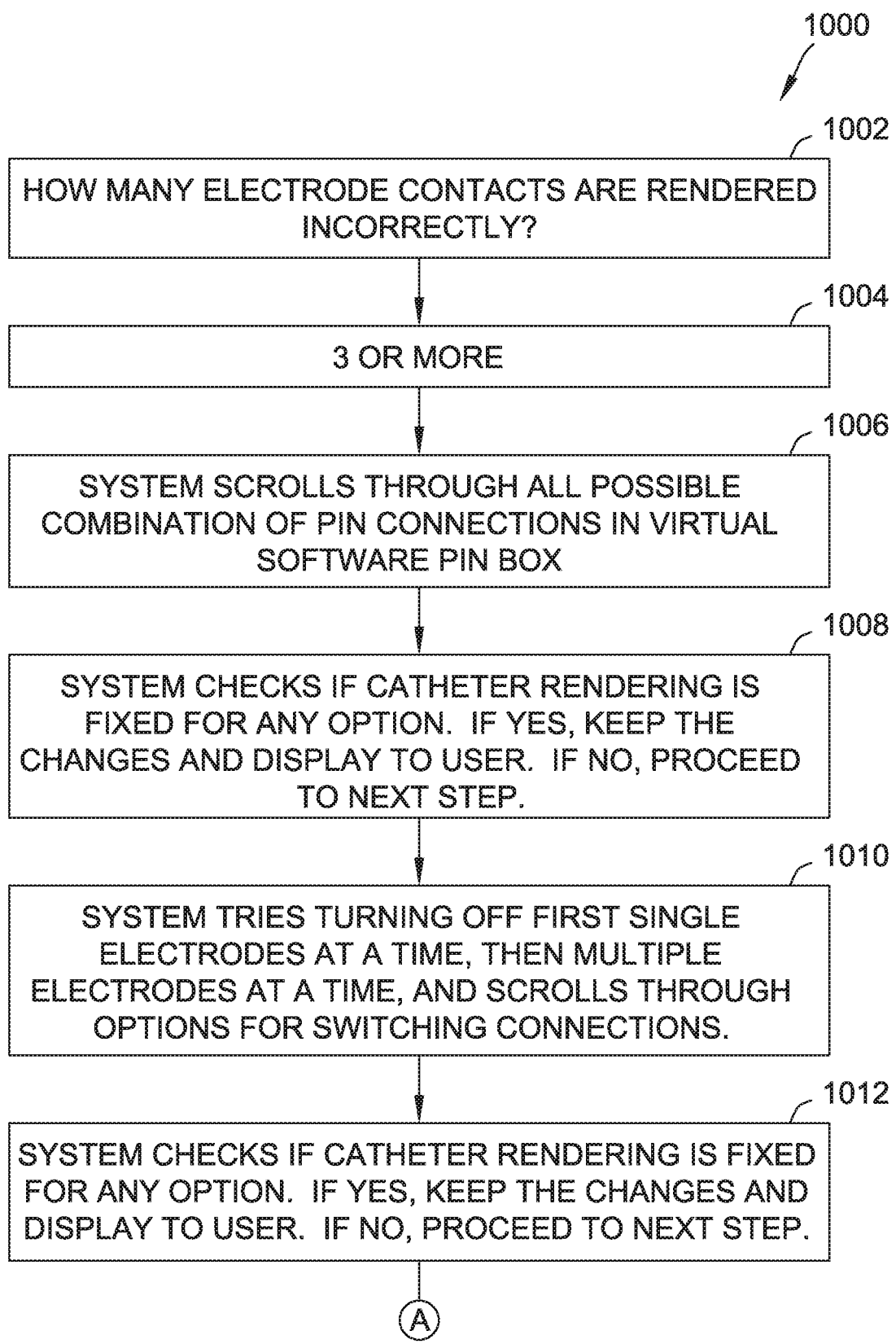
FIGS. 10A and 10B are a flowchart of a method for automatically troubleshooting a catheter rendering issue when three or more electrodes are being rendered incorrectly.
Figure 10B:
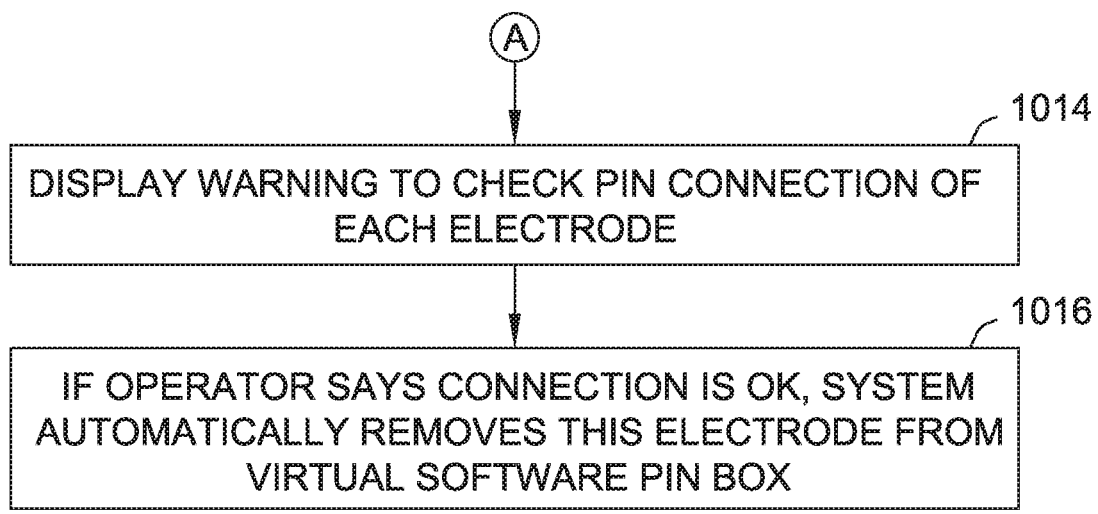

FIGS. 10A and 10B are a flowchart of a method 1000 for automatically troubleshooting a catheter rendering issue when three or more electrodes 30 are being rendered incorrectly. As shown in FIG. 1000, ECU 100 initially determines 1002 how many electrodes 30 rendered incorrectly, and makes 1004 the determination that three or more electrodes 30 are rendered incorrectly.

When three or more electrodes 30 are rendered incorrectly, it is likely that the catheter pins for at least two of the three or more electrodes 30 are switched relative to the sockets for those at least two electrodes 30. Accordingly, ECU 100 automatically switches, or cycles, 1006 through all of the possible permutations of connections for the three or more electrodes 30 in the virtual pin box. For example, if electrodes A, B, and C are rendered incorrectly, ECU 100 tries switching the connections for electrodes A and B, switching the connections for electrodes A and C, and switching the connections for electrodes B and C. For each permutation, ECU 100 checks 1008 whether the rendering issue is at least partially resolved. If the rendering issue is partially or fully resolved, ECU 100 maintains the changes to the virtual pin box, and displays the changes (e.g., on display device 102).

If the rendering issue is not fully resolved, ECU 100 further attempts to address the rendering issue by selectively deactivating 1010, one at a time, the electrodes 30 that are rendering incorrectly and cycles through all of the possible permutations of connections for the remaining electrodes 30 that are rendering incorrectly in the virtual pin box. Further, in one embodiment, ECU 100 then deactivates multiple electrodes 30 that are rendering incorrectly and cycles through all of the possible permutations of connections for the remaining electrodes 30 that are rendering incorrectly in the virtual pin box. Again, for each permutation, ECU 100 checks 1012 whether the rendering issue is at least partially resolved. If the rendering issue is partially or fully resolved, ECU 100 maintains the changes to the virtual pin box, and displays the changes (e.g., on display device 102).

If the rendering issue is still not fully resolved, ECU 100 displays 1014 a warning on display device 102. The warning instructs the operator to check the connections between the catheter pin and the socket associated with each of the remaining incorrectly rendered electrodes 30. For example, upon checking, the operator may determine that the catheter pins for each of the remaining incorrectly rendered electrodes 30 are disconnected or otherwise faulty. Accordingly, the operator may proceed to fix the connections at least some of the remaining incorrectly rendered electrodes 30, partially or fully resolving the rendering issue.

If, however, the operator verifies that the catheter pin for at least one of the remaining incorrectly rendered electrodes 30 is connected properly (e.g., by user input to ECU 100), it is likely that the at least one electrode 30 of the remaining incorrectly rendered electrodes 30 is faulty, and unlikely that the catheter pin is plugged into the incorrect socket for the at least one electrode 30 of the remaining incorrectly rendered electrodes 30. Accordingly, in this situation, ECU 100 automatically removes 1016 the at least one electrode 30 of the remaining incorrectly rendered electrodes 30 from the virtual pin box, such that the at least one electrode 30 is no longer used when rendering catheter 16.

Accordingly, in the embodiments described herein, ECU 100 determines that catheter 16 is being rendered incorrectly, and carries out an automated procedure to address the rendering issue. This substantially reduces the time and effort required to identify and resolve rendering issues.

It should be understood that system 10, and particularly ECU 100, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system comprising:
a catheter comprising a plurality of electrodes and a plurality of catheter pins, each catheter pin corresponding to an associated electrode of the plurality of electrodes; and
a mapping system communicatively coupled to the catheter, the mapping system comprising:
a pin box comprising a plurality of sockets corresponding to the plurality of catheter pins;
a display device configured to render the catheter; and
an electronic control unit (ECU) communicatively coupled to the display device and the pin box, the ECU configured to:
determine that the catheter is being rendered incorrectly on the display device;
determine a number of electrodes that are being rendered incorrectly on the display device;
identify at least one particular electrode of the plurality of electrodes that is being rendered incorrectly; and
attempt to resolve, using a virtual pin box controllable by the ECU, the incorrect rendering of the catheter automatically based on the determined number of electrodes and the at least one particular electrode, wherein the virtual pin box is configured to electronically switch functions of the plurality of sockets in the pin box while the plurality of catheter pins remain physically connected to the same sockets.

2. The system of claim 1, wherein to determine that the catheter is being rendered incorrectly, the ECU is configured to determine that the catheter is being rendered incorrectly based on a user input received at the ECU.

3. The system of claim 1, wherein to determine that the catheter is being rendered incorrectly, the ECU is configured to determine that the catheter is being rendered incorrectly by automatically comparing a shape of the rendered catheter as it appears on the display device to an expected catheter shape.

4. The system of claim 1,
wherein to determine a number of electrodes, the ECU is configured to determine that one electrode is being rendered incorrectly;
wherein to identify at least one particular electrode, the ECU is configured to identify a single particular electrode; and
wherein to attempt to resolve the incorrect rendering, the ECU is configured to:
cause a warning to be displayed on the display device, the warning instructing an operator to verify a connection between a first catheter pin that corresponds to the single particular electrode and a first socket that corresponds to the first catheter pin.

5. The system of claim 4, wherein the ECU is further configured to:
receive a user input verifying the connection between the first catheter pin and the first socket; and
remove, based on the user input, the single particular electrode and the first catheter pin from the virtual pin box, such that the single particular electrode is no longer used to render the catheter even though the first catheter pin is still physically connected to the first socket.

6. The system of claim 1,
wherein to determine a number of electrodes, the ECU is configured to determine that two electrodes are being rendered incorrectly;
wherein to identify at least one particular electrode, the ECU is configured to identify two particular electrodes; and
wherein to attempt to resolve the incorrect rendering, the ECU is configured to:
  switch connections on the virtual pin box between two sockets that are associated with the two particular electrodes while the plurality of catheter pins remain physically connected to the same sockets;
  determine whether the switched connections resolve the incorrect rendering; and
  if the switched connections do not resolve the incorrect rendering:
    switch the connections again between the two sockets on the virtual pin box; and
    cause a warning to be displayed on the display device, the warning instructing an operator to verify connections associated with the two particular electrodes.

7. The system of claim 1,
wherein to determine a number of electrodes, the ECU is configured to determine that at least three electrodes are being rendered incorrectly;
wherein to identify at least one particular electrode, the ECU is configured to identify at least three particular electrodes; and
wherein to attempt to resolve the incorrect rendering, the ECU is configured to:
  switch through different permutations of connections on the virtual pin box for at least three sockets that are associated with the at least three particular electrodes while the plurality of catheter pins remain physically connected to the same sockets; and
  determine whether the switched connections resolve the incorrect rendering.

8. A computer-implemented method for resolving catheter rendering issues in a system including a catheter having a plurality of electrodes and a plurality of catheter pins, each catheter pin corresponding to an associated electrode of the plurality of electrodes, the system further including a mapping system including a pin box including a plurality of sockets corresponding to the plurality of catheter pins, a display device configured to render the catheter, and an electronic control unit (ECU) communicatively coupled to the display device and the pin box, and a virtual pin box, the ECU generating display signals for the display device, the method comprising:
  determining, by the ECU, that the catheter is being rendered incorrectly on the display device;
  determining, by the ECU, a number of electrodes that are being rendered incorrectly on the display device;
  identifying, by the ECU, at least one particular electrode of the plurality of electrodes that is being rendered incorrectly on the display device; and
  attempting, by the ECU, to resolve, using a virtual pin box controllable by the ECU, the incorrect rendering of the catheter based on the determined number of electrodes and the at least one particular electrode, wherein the virtual pin box is configured to electronically switch functions of the plurality of sockets in the pin box while the plurality of catheter pins remain physically connected to the same sockets.

9. The method of claim 8, wherein determining that the catheter is being rendered incorrectly comprises determining that the catheter is being rendered incorrectly based on a user input received at the ECU.

10. The method of claim 8, wherein determining that the catheter is being rendered incorrectly comprises determining that the catheter is being rendered incorrectly by automatically comparing a shape of the rendered catheter as it appears on the display device to an expected catheter shape.

11. The method of claim 8,
wherein determining a number of electrodes comprises determining that one electrode is being rendered incorrectly;
wherein identifying at least one particular electrode comprises identifying a single particular electrode; and
wherein attempting to resolve the incorrect rendering comprises:
  causing a warning to be displayed on the display device, the warning instructing an operator to verify a connection between a first catheter pin that corresponds to the single particular electrode and a first socket that corresponds to the first catheter pin;
  receiving a user input verifying the connection between the first catheter pin and the first socket; and
  removing, based on the user input, the single particular electrode and the first catheter pin from the virtual pin box, such that the single particular electrode is no longer used to render the catheter even though the first catheter pin is still physically connected to the first socket.

12. The method of claim 8,
wherein determining a number of electrodes comprises determining that two electrodes are being rendered incorrectly;
wherein identifying at least one particular electrode comprises identifying two particular electrodes; and
wherein attempting to resolve the incorrect rendering comprises:
  switching connections on the virtual pin box between two sockets that are associated with the two particular electrodes while the plurality of catheter pins remain physically connected to the same sockets box;
  determining whether the switched connections resolve the incorrect rendering; and
  if the switched connections do not resolve the incorrect rendering:
    switching the connections again between the two sockets on the virtual pin box; and
    causing a warning to be displayed on the display device, the warning instructing an operator to verify connections associated with the two particular electrodes.

13. The method of claim 8,
wherein determining a number of electrodes comprises determining that at least three electrodes are being rendered incorrectly;
wherein identifying at least one particular electrode comprises identifying at least three particular electrodes; and
wherein attempting to resolve the incorrect rendering comprises:
  switching through different permutations of connections on the virtual pin box for at least three sockets that are associated with the at least three particular electrodes while the plurality of catheter pins remain physically connected to the same sockets; and determining whether the switched connections resolve the incorrect rendering.

14. A processing apparatus for resolving catheter rendering issues in a system including a catheter having a plurality of electrodes and a plurality of catheter pins, each catheter pin corresponding to an associated electrode of the plurality of electrodes, the system further including a mapping system including a pin box including a plurality of sockets corresponding to the plurality of catheter pins, and a display device configured to render the catheter, the processing apparatus communicatively coupled to the display device and the pin box and configured to:
   determine that the catheter is being rendered incorrectly on the display device;
   determine a number of electrodes that are being rendered incorrectly on the display device;
   identify at least one particular electrode of the plurality of electrodes that is being rendered incorrectly on the display device; and
   attempt to resolve, using a virtual pin box, the incorrect rendering of the catheter based on the determined number of electrodes and the at least one particular electrode, wherein the virtual pin box is configured to electronically switch functions of the plurality of sockets in the pin box while the plurality of catheter pins remain physically connected to the same sockets.

15. The processing apparatus of claim 14, wherein to determine that the catheter is being rendered incorrectly, the processing apparatus is configured to determine that the catheter is being rendered incorrectly based on a user input received at the processing apparatus.

16. The processing apparatus of claim 14, wherein to determine that the catheter is being rendered incorrectly, the processing apparatus is configured to determine that the catheter is being rendered incorrectly by comparing a shape of the rendered catheter to an expected catheter shape.

17. The processing apparatus of claim 14,
   wherein to determine a number of electrodes, the processing apparatus is configured to determine that one electrode is being rendered incorrectly;
   wherein to identify at least one particular electrode, the processing apparatus is configured to identify a single particular electrode; and
   wherein to attempt to resolve the incorrect rendering, the processing apparatus is configured to:
      cause a warning to be displayed on the display device, the warning instructing an operator to verify a connection between a first catheter pin that corresponds to the single particular electrode and a first socket that corresponds to the first catheter pin.

18. The processing apparatus of claim 17, wherein the processing apparatus is further configured to:
   receive a user input verifying the connection between the first catheter pin and the first socket; and
   remove, based on the user input, the single particular electrode and the first catheter pin from the virtual pin box, such that the single particular electrode is no longer used to render the catheter even though the first catheter pin is still physically connected to the first socket.

19. The processing apparatus of claim 14,
   wherein to determine a number of electrodes, the processing apparatus is configured to determine that two electrodes are being rendered incorrectly;
   wherein to identify at least one particular electrode, the processing apparatus is configured to identify two particular electrodes; and
   wherein to attempt to resolve the incorrect rendering, the processing apparatus is configured to:
      switch connections on the virtual pin box between two sockets that are associated with the two particular electrodes while the plurality of catheter pins remain physically connected to the same sockets;
      determine whether the switched connections resolve the incorrect rendering; and
      if the switched connections do not resolve the incorrect rendering:
         switch the connections again between the two sockets; and
         cause a warning to be displayed on the display device, the warning instructing an operator to verify connections associated with the two particular electrodes.

20. The processing apparatus of claim 14,
   wherein to determine a number of electrodes, the processing apparatus is configured to determine that at least three electrodes are being rendered incorrectly;
   wherein to identify at least one particular electrode, the processing apparatus is configured to identify at least three particular electrodes; and
   wherein to attempt to resolve the incorrect rendering, the processing apparatus is configured to:
      switch through different permutations of connections on the virtual pin box for at least three sockets that are associated with the at least three particular electrodes while the plurality of catheter pins remain physically connected to the same sockets; and
      determine whether the switched connections resolve the incorrect rendering.

\* \* \* \* \*